US010189805B2

(12) United States Patent
Manning et al.

(10) Patent No.: US 10,189,805 B2
(45) Date of Patent: Jan. 29, 2019

(54) METABOLISM PROBES FOR THERAPY AND DIAGNOSIS

(71) Applicant: Vanderbilt University, Nashville, TN (US)

(72) Inventors: H. Charles Manning, Nashville, TN (US); Michael Schulte, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/510,217

(22) PCT Filed: Sep. 9, 2015

(86) PCT No.: PCT/US2015/049252
§ 371 (c)(1),
(2) Date: Mar. 9, 2017

(87) PCT Pub. No.: WO2016/040527
PCT Pub. Date: Mar. 17, 2016

(65) Prior Publication Data
US 2017/0283387 A1  Oct. 5, 2017

Related U.S. Application Data

(60) Provisional application No. 62/047,960, filed on Sep. 9, 2014.

(51) Int. Cl.
*C07C 237/04* (2006.01)
*C07C 237/10* (2006.01)
*A61K 31/167* (2006.01)
*C07D 295/26* (2006.01)
*C07D 277/66* (2006.01)
*C07D 295/135* (2006.01)
*C07D 213/40* (2006.01)
*C07D 207/325* (2006.01)
*C07D 235/18* (2006.01)

(52) U.S. Cl.
CPC .......... *C07D 295/26* (2013.01); *A61K 31/167* (2013.01); *C07C 237/04* (2013.01); *C07C 237/10* (2013.01); *C07D 207/325* (2013.01); *C07D 213/40* (2013.01); *C07D 235/18* (2013.01); *C07D 277/66* (2013.01); *C07D 295/135* (2013.01)

(58) Field of Classification Search
CPC .............................. C07C 237/04; C07C 237/10
See application file for complete search history.

(56) References Cited

U.S. PATENT DOCUMENTS 5,686,486 A * 11/1997 Tomich ................ C07D 311/56
514/210.19
2013/0065935 A1  3/2013 Esslingers et al.

FOREIGN PATENT DOCUMENTS

WO   WO19900003399 A1   4/1990

OTHER PUBLICATIONS

Dikov, Bulgarska Akademiya na Naukite, 1999, vol. 52(7-8), p. 93-96.*
Golub, 1999, Science, vol. 286, p. 531-537.*
Cancer Prevention, downloaded from http://www.cancer.gov/cancertopics/pdq/prevention/overview/patient on Nov. 14, 2012.*
Targeted Cancer Therapies Fact Sheet, retrieved from http://www.cancer.gov/about-cnacer/treatment/types/targeted-therapies/targeted-therapies-fact-sheet on Dec. 8, 2015.*
Itoh, Chem Pharm, Bull, vol. 44, No. 8, p. 1498-1509. (Year: 1996).*
CAS record for DN 128:34683, access No. 1997:739374. (Year: 1997).*
CAS Reg No. 1348071-88-4, entered into STN Dec. 4, 2011 (Year: 2011).*
Vargha, et al, Synthesis of some gamma-glutamyl amides, Studia Universitatis Babes-Bolyai, Chemia, vol. 26, Issue 2, p. 43-46. (Year: 1981).*
Agdeppa, Review of Imaging Agent Development, Jun. 2009, AAPS Journal, vol. 11, No. 2, p. 286-299. (Year: 2009).*
PubChem Substance summary for CID 10542520 Deposit date Oct. 25, 2006.
Esslinger et al. N-Glutamine Analogues as Probes of the ASCT2 Neutral Amino Acid Transporter Binding Site in Bioorganic and Medicinal Chemistry, 2005, vol. 13, pp. 1111-1118.
Albers, et al., Defining Substrate and Blocker Activity of Alanine-Serine-Cysteine Transporter 2 (ASCT2) Ligands with Novel Serine Analogs; Mol. Pharmacol.; 2012, 81(3), 356-365.
Brown, et al., In vitro characterization of a small molecule inhibitor of the alanine serine cysteine transporter-1 (SLC7A10); J. Neurochem.; 2014, 129(2), 275-283.
Dang, C. V., Rethinking the Warburg Effect with Myc Micromanaging Glutamine Metabolism; Cancer Research, 2010, 70, 859.
Dang, et al., MYC-Induced Cancer Cell Energy Metabolism and Therapeutic Opportunities; Clinical Cancer Research, 2009, 15, 6479.
Fuchs, et al., Inducible antisense RNA targeting amino acid transporter ATB0/ASCT2 elicits apoptosis in human hepatoma cells; Am. J. Physiol. Gastrointest. Liver Physiol. 2004, 286(3), G467-G478.
Gaglio, et al., Oncogenic K-Ras decouples glucose and glutamine metabolism to support cancer cell growth; Molecular systems biology, 2011, 7, 523.
Hassanein, et al., SLC1A5 Mediates Glutamine Transport Required for Lung Cancer Cell Growth and Survival; Clin. Cancer Res. 2013, 19(3), 560-570.

(Continued)

*Primary Examiner* — Rebecca L Anderson
*Assistant Examiner* — Karen Cheng
(74) *Attorney, Agent, or Firm* — Stites & Harbison PLLC; Richard S. Myers, Jr.

(57) ABSTRACT

Novel 2-substituted glutamylanides useful as modulators of ASCT2 inhibitors. Compounds of the present invention can be used to treat patients suffering from diseases caused or influenced by abnormal ASCT2 transporter dysfunction.

13 Claims, No Drawings

(56) References Cited

OTHER PUBLICATIONS

Kaira, et al., Clinicopathological significance of ASC amino acid transporter-2 expression in pancreatic ductal carcinoma; Histopathology; 2015; pp. 235-243.
Shimizu, et al., ASC amino-acid transporter 2 (ASCT2) as a novel prognostic marker in non-small cell lung cancer; British Journal of Cancer, 2014, 110, 2030-2039.
Watanabe, et al., Differential gene expression signatures between colorectal cancers with and without KRAS mutations: Crosstalk between the KRAS pathway and other signalling pathways; Eur. J. Cancer, 2011, 47, 1946.
Witte, et al., Overexpression of the Neutral Amino Acid Transporter ASCT2 in Human Colorectal Adenocarcinoma; Anticancer Research; 2002, 22(5), 2555-2557.

* cited by examiner

METABOLISM PROBES FOR THERAPY AND DIAGNOSIS

PRIOR APPLICATIONS

This application claims priority from International Patent Application No. PCT/US2015/049252 filed Sep. 9, 2015 which claims benefit to U.S. Provisional Patent Application Ser. No. 62/047,960 which was filed on Sep. 9, 2014, the entire disclosures of which are incorporated herein by this reference.

BACKGROUND OF THE INVENTION

The ASCT2 (SLC1A5) transporter is a transporter of neutral amino acids such as glutamine and a range of other neutral amino acids (such as glutamine, leucine, and isoleucine) in and out of a cell in a $Na^+$ dependent, obligate amino acid exchange process. These transporters, by shuttling of various amino acids across the cell membrane, may facilitate or regulate various physiological processes such as cell growth, proliferation, or even glutamatergic neurotransmission via the glutamate/glutamine cycle.

Emerging evidence implicates oncogenic signaling pathways with nutrient uptake in cancer cells. The natural amino acid glutamine is essential for cell growth and proliferation. In addition to glucose, cancer cells utilize glutamine as a carbon source for ATP production and biosynthesis. Mammalian cells internalize glutamine through an evolutionary redundant repertoire of cell surface transporters though a primary sodium-dependent transporter of glutamine. ASCT2 (gene symbol SLC1A5), stands out as a promising target for probe development. In cancer cells, SLC1A5 expression is associated with oncogenic MYC and KRAS, suggesting its relevance in many clinically important tumors, including lung, colon, and pancreas. It has been previously demonstrated that that SLC1A5 antisense RNA triggered apoptosis in human hepatocellular carcinoma cells. See Fuchs et al., Am. J. Physiol. Gastrointest. Liver Physiol. 2004, 286(3), G467-G478. Similarly, it has been reported that SLC1A5 was expressed in 95% of squamous cell carcinomas (SCC), 74% of adenocarcinomas (ADC), and 50% of neuroendocrine tumors. Further, siRNA down regulation of ASCT2 in lung cancer cells resulted in significant growth inhibition. See Hassanein et al., Clin. Cancer Res. 2013, 19(3), 560-570. Collectively, these studies suggest that the discovery of small molecules capable of inhibiting ASCT2 activity represents an important area in the development of precision cancer medicines.

Accordingly, ASCT2 inhibitors, can be used as pharmacologic research tools to inhibit and investigate ASCT2-mediated amino acid transport and function. Such inhibitors can be used as chemotherapeutic agents alone or in combination with other chemotherapeutic agents to treat various human or mammalian tumors or cancers. These compounds can be used as anti-metabolite agents alone or in combination with other chemotherapeutic agents to slow or prevent growth of various human or mammalian tumors and they can serve as effective anti-microbial agents to suppress growth of various pathogenic microbes.

Unfortunately, few pharmacological inhibitors of ASCT2 have been reported. In 2004, Esslinger described L-γ-glutamyl-p-nitroanilide (GPNA) as a commercially available probe of the ASCT2 amino acid binding site. While this work describes potential electronic requirements for binding to ASCT2 through alteration of the amide N—H $pK_a$ via simple aryl substitutions, it did not address the steric requirements for binding to ASCT2 within this compound class.

Thus, a need remains for additional inhibitors of ASCT transporters that can be used as pharmacologic tools to evaluate the physiologic significance of the ASCT transporter by pharmacologic intervention and thus better understand its role in various biologic pathways.

SUMMARY OF THE INVENTION

Embodiments of the present invention include the discovery and structure-activity relationships (SAR) of 2-substituted glutamylanilides as probes of the steric environment comprising the amino acid binding domain of alanine-serine-cysteine transporter subtype 2 (ASCT2). As an example, the present invention includes the novel probe N-(2-(morpholinomethyl)phenyl)-L-glutamine, which was found to have an $IC_{50}$ of 312 μM in a $^3$H-glutamine uptake assay. This represents a threefold improvement over the most potent previously reported inhibitor in this series, GPNA, a superior and unexpected result.

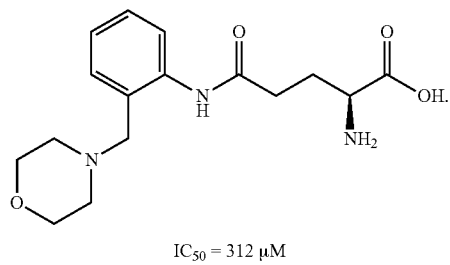 [SMILES: N[C@@H](CCC(=O)Nc1ccccc1CN1CCOCC1)C(=O)O]

$IC_{50} = 312$ μM

Other non-limiting examples include the following compounds:

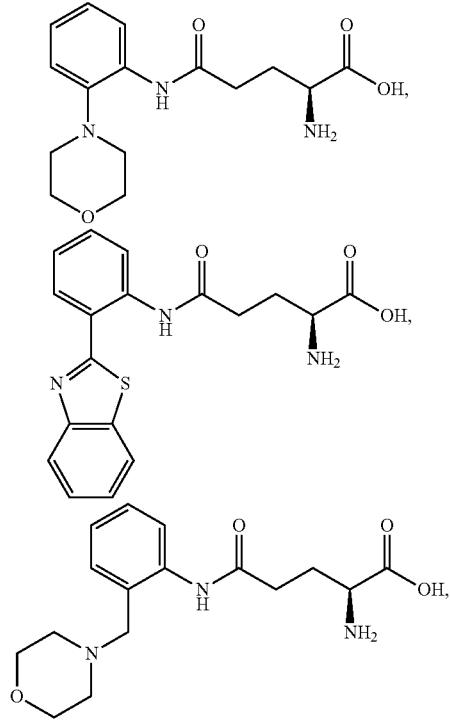

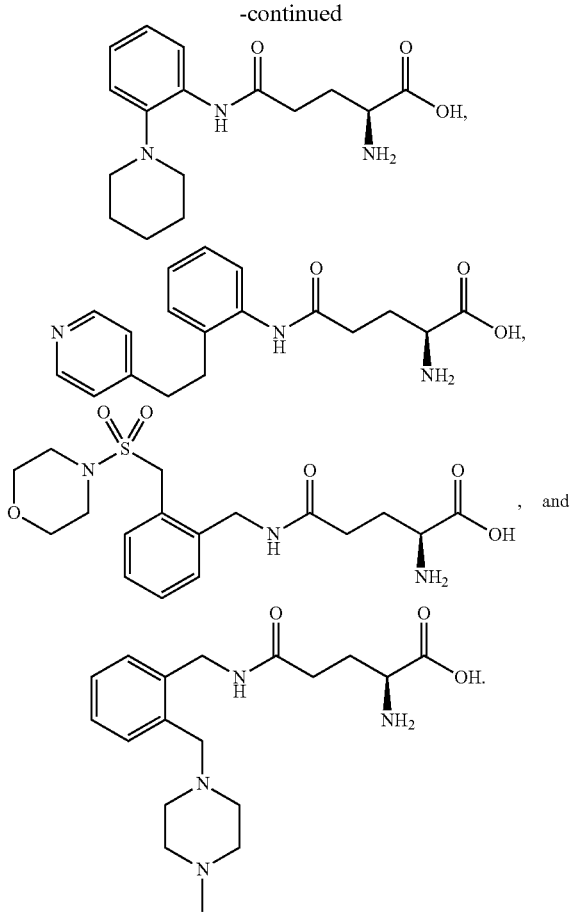

The present invention also includes pharmaceutical compounds that comprise compounds of the present invention.

The present invention also includes methods for treating cancer. The compounds of the present invention can be used as chemotherapeutic agents alone or in combination with other chemotherapeutic agents to treat various human or mammalian tumors or cancers.

The present invention also includes methods for sensitizing cancer treatment.

The present invention also includes methods of treating microbial infection.

The present invention also includes methods of treating ischemia-related central nervous system injury.

The present invention also includes methods of medical imaging.

DESCRIPTION OF EMBODIMENTS OF THE PRESENT INVENTION

As indicated herein, embodiments of the present invention include the discovery of ASCT2 inhibitors. The compounds of the present invention accomplish that need. As such, the compounds of the present invention can be used as modulators of ASCT2 transporters.

The compounds of the present invention can also be used to treat patients (e.g., humans) suffering from diseases, conditions, disorders, or syndromes caused or influenced by abnormal ASCT2 transporter dysfunction. Such diseases, conditions, disorders, and syndromes include, e.g., cancer, microbial infections, and ischemia-related central nervous system (CNS) injuries.

The compounds of the present invention can also be used to treat ASCT2 functional abnormalities.

The compounds of the present invention can also contain a radionuclide, such as fluorine-18, for use in radiographic medical imaging applications in a patient (e.g., human) to diagnose or follow the progression of diseases, disorders, conditions, or symptoms related to a disease, disorder, condition, or symptom caused or related to ASCT2 functional abnormality, including, but not limited to, cancer, microbial infections, and ischemia-related central nervous symptom injuries.

In summary, embodiments of the present invention includes novel Nγ-glutamylanilides as inhibitors of cellular glutamine uptake via ASCT2 with significantly greater potency than GPNA. Evaluation of this chemical series within the context of ligand docking to a homology model of human ASCT2 revealed compatibility with the ASCT2 binding site based on SurflexDock Total Scores. The data show that compounds of the present invention interact with multiple structural elements within the ASCT2 binding site, including the amino acid zwitter ion binding site and the adjacent hydrophobic pocket. Uniquely, previous work in the Nγ-glutamylanilide series suggested that reduction of the glutamine amide $pK_a$ was required for ASCT2 inhibition; the present inventors did not observe this trend.

Unless defined otherwise, all technical and scientific terms used herein have the meaning commonly understood by a person skilled in the art.

As used herein, the singular form "a," "an," and "the" include plural references unless the context clearly dictates otherwise. For example, the term "a cell" includes a plurality of cells, including mixtures thereof.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3SH$, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$3), fully substituted (e.g., —$CF_2$2$CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Optical isomers are compounds with the same molecular formula but differ in the way they rotate plane polarized light. There are two types of optical isomers. The first type of optical isomers are compounds that are mirror images of one another but cannot be superimposed on each other. These isomers are called "enantiomers." The second type of optical isomers are molecules that are not mirror images but each molecule rotates plane polarized light and are considered optically-active. Such molecules are called "diastereoisomers." Diastereoisomers differ not only in the way they rotate plane polarized light, but also their physical properties. The term "optical isomer" comprises more particularly the enantiomers and the diastereoisomers, in pure form or in the form of a mixture.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "cancer" refers to or describes the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer. Particular, but non-limiting examples of the present invention is lung, colon, and pancreatic cancer.

The terms "combination therapy" or "co-administration" mean the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "imaging agent" as used herein refers to any moiety useful for the detection, tracing, or visualization of a compound of the invention when coupled thereto. Imaging agents include, e.g., an enzyme, a fluorescent label (e.g., fluorescein), a luminescent label, a bioluminescent label, a magnetic label, a metallic particle (e.g., a gold particle), a nanoparticle, an antibody or fragment thereof (e.g., a Fab, Fab', or F(ab'), molecule), and biotin. An imaging agent can be coupled to a compound of the invention by, for example, a covalent bond, ionic bond, van der Waals interaction or a hydrophobic bond. An imaging agent of the invention can be a radiolabel coupled to a compound of the invention, or a radioisotope incorporated into the chemical structure of a compound of the invention. Methods of detecting such imaging agents are well known to those having skill in the art.

The phrase "therapeutically effective" is intended to qualify the amount of active ingredients used in the treatment of a disease or disorder. This amount will achieve the goal of reducing or eliminating the disease or disorder.

The term "therapeutically acceptable" refers to those compounds (or salts, esters, prodrugs, tautomers, zwitterionic forms, etc. thereof) which are suitable for use in contact with the tissues of patients without undue toxicity, irritation, and allergic response, are commensurate with a reasonable benefit/risk ratio, and are effective for their intended use.

As used herein, the term "subject" refers to a target of administration. The subject of the herein disclosed methods can be a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder, preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by a modulation of Ras signaling" means having been subjected to a physical examination by a person of skill, for example, a physician, and found to have a condition that can be diagnosed or treated by a compound or composition that can modulate Ras signaling. Such a diagnosis can be in reference to a disorder, such as cancer, and the like, as discussed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "cancer" refers to disorders characterized by cellular proliferation, evasion of programmed cell death, altered cellular metabolism, induction of angiogenesis, enhancement of cellular invasion and metastasis, alterations to tumor suppressor genes causing a reduction in activity, alterations to oncogenes casing enhancement of activity, or evasion of immunological destruction. Cancer can refer to a tissue or organ type and can also spread from one tissue or organ to another tissue type or organ. Cancer can occur in any cell of any type including but not limited to breast, prostate, skin, lung, pancreatic, stomach, brain, kidney, uterine, ovarian, testicular, endothelial, colon, bladder, bone as well as cells of the blood to produce various forms of leukemia.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents. Unless otherwise specified, the substituents are all independent from one another.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, thioether, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "heterocycle," as used herein refers to single and multi-cyclic aromatic or non-aromatic ring systems in which at least one of the ring members is other than carbon. Heterocycle includes pyridinde, pyrimidine, pyrazine, furan, thiophene, pyrrole, isoxazole, isothiazole, pyrazole, oxazole, thiazole, imidazole, oxazole, oxadiazole including, for example, 1,2,3-oxadiazole, 1,2,5-oxadiazole and 1,3,4-oxadiazole,thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, imidazothiadiazole, imidazooxadiazole, imidazothiazole, thiazolotriazole, and the like.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

In some aspects, a structure of a compound can be represented by a formula:

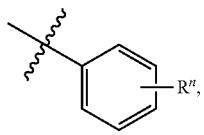

which is understood to be equivalent to a formula:

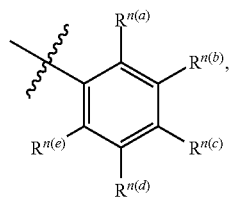

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance. Likewise, when a group R is defined as four substituents, R is understood to represent four independent substituents, $R^a$, $R^b$, $R^c$, and $R^d$. Unless indicated to the contrary, the substituents are not limited to any particular order or arrangement.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Compounds

In one aspect, the invention relates to compounds, or pharmaceutically acceptable derivatives thereof, useful as modulators of Ras signaling. In general, it is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

In one aspect the invention relates to compounds having a structure represented by formula:

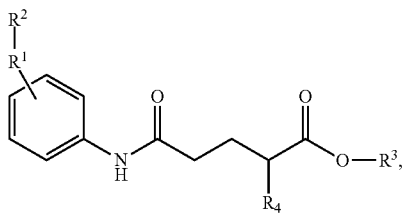

wherein $R^1$ is a bond, optionally substituted $C_1$-$C_6$ alkyl, or optionally substituted $SO_2$—($C_1$-$C_6$ alkyl); $R^2$ is optionally substituted aryl, optionally substituted heteroaryl, optionally substituted heterocycle, or optionally substituted heterocycloalkyl; $R^1$ is H or optionally substituted $C_1$-$C_6$ alkyl; and $R^4$ is $NH_2$ or NHBoc; or pharmaceutically acceptable salts or derivatives thereof.

In other embodiments of the present invention, $R^1$ is a bond, —$CH_2$—, or —$CH_2$—$CH_2$—.

In other embodiments of the present invention, $R^2$ is optionally substituted phenyl or $R^2$ is optionally substituted and chosen from morpholino, pyrrolidine, pyrrole, piperidine, pyridine, benzoimidizole, benzothiazole, piperizine, methyl-piperizine, or pyridine.

In other embodiments of the present invention, $R^2$ is chosen from:

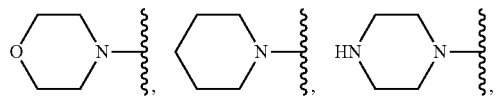

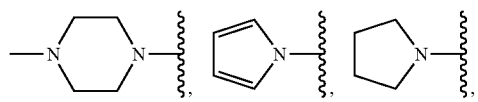

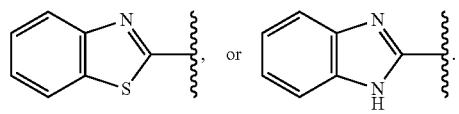

In other embodiments of the present invention, $R^2$ is —H or

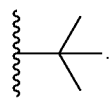

Exemplary compounds of the present invention include the following:

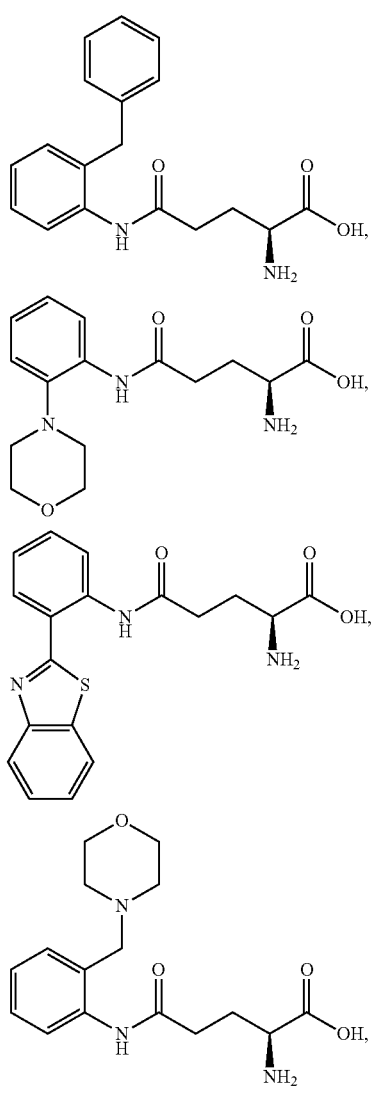
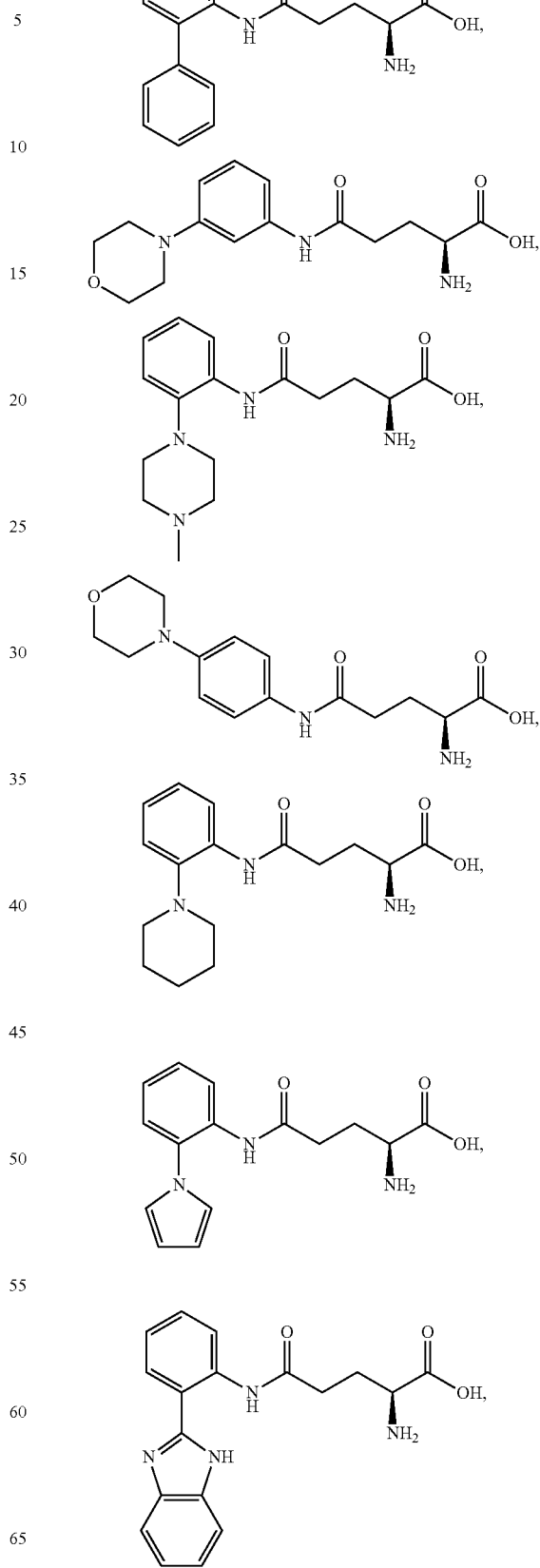

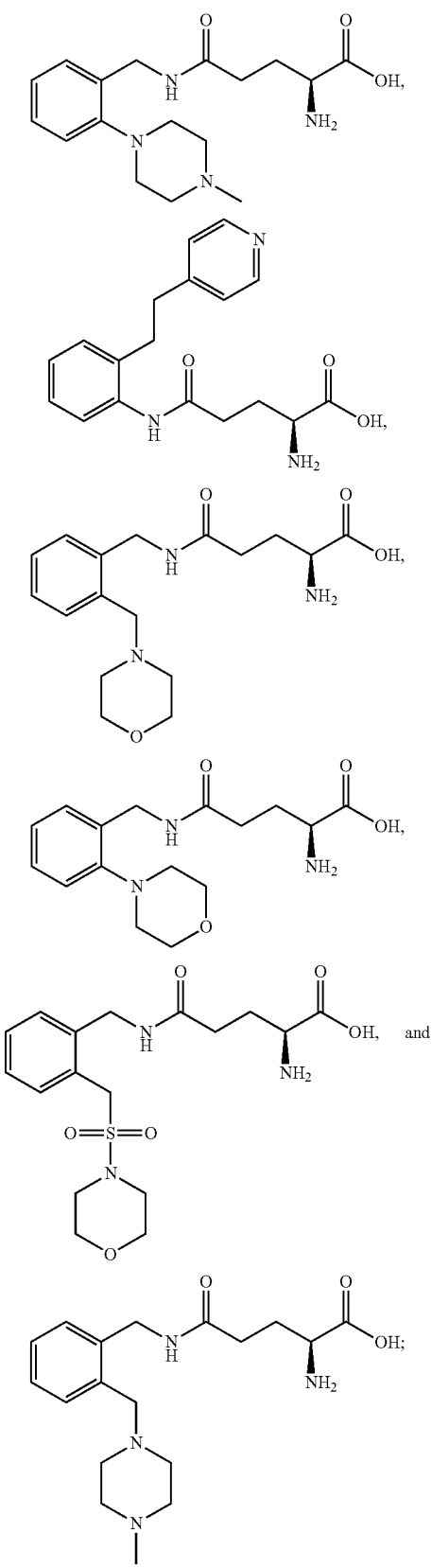

or pharmaceutically acceptable salts or derivatives thereof.

Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds. The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

It is understood that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

Further disclosed herein are pharmaceutical compositions comprising one or more of the disclosed modulators of Ras signaling and a pharmaceutically acceptable carrier.

Accordingly, the pharmaceutical compositions of the present invention include those that contain one or more other active ingredients, in addition to a compound of the present invention.

The above combinations include combinations of a disclosed compound not only with one other active compound, but also with two or more other active compounds. Likewise, disclosed compounds may be used in combination with other drugs that are used in the prevention, treatment, control, amelioration, or reduction of risk of the diseases or conditions for which disclosed compounds are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient can be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent may be co-administered, either in concomitant therapy or in a fixed combination.

In one aspect, the compound can be employed in combination with at least one additional therapeutic agent. In one aspect of the invention the at least one additional therapeutic agent may be a cancer chemotherapeutic agent. In one aspect, the chemotherapeutic agent(s) may be platinum compounds, topoisomerase inhibitors, peptide antibiotics, alkylators, anthrcyclines, taxenes, histone deacetylase inhibitors, epothilones, kinase inhibitors, nucleotide analogues, retinoids, vinca alkaloids and derivatives, or any combination of chemotherapeutics. The platinum compound(s) may be carboplatin, cisplatin, or oxaliplatin. The topoisomerase inhibitor(s) may be irinotecan, topotecan, etoposide, teniposide, or tafluposide. The peptide antibiotic(s) may be bleomycin or actinomycin. The alkylator(s) may be cyclophosphamide, mechlorethamine, chlorambucil, or melphalan. The anthracycline(s) may be daunorubicin, doxorubicin, epirubicin, mitoxntrone, or valirubicin. The taxene(s) may be paclitaxel or docetaxel. The histone deacetylase inhibitor(s) may be vorinostat or romidepsin. The epothilone(s) may be ixabepilone, patupilone, or sagopilone. The kinase inhibitor(s) may be borteomib, dabrafenib, erlotinib, gefitinib, imatinib, tremetinib, vemurafenib, or vismodegib.

The nucleotide analogue(s) may be azacitidine, azathioprine, capecitabine, cytarabine, flurouracil, gemcitabine, hydroxyurea, mercaptopurine, methotrexate, or tioguanine.

In one aspect, the invention relates to pharmaceutical compositions comprising a compound having a structure represented by a formula:

In one aspect the invention relates to compounds having a structure represented by formula:

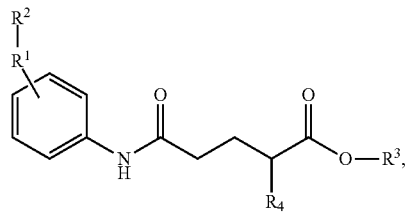

wherein $R^1$ is a bond, optionally substituted $C_1$-$C_6$ alkyl, or optionally substituted $SO_2$—($C_1$-$C_6$ alkyl); $R^1$ is optionally substituted aryl, optionally substituted heteroaryl, optionally substituted heterocycle, or optionally substituted heterocycloalkyl; $R^1$ is H or optionally substituted $C_1$-$C_6$ alkyl; and $R^4$ is $NH_2$ or NHBoc; or pharmaceutically acceptable salts or derivatives thereof.

Methods of Use

The compounds of the invention can be used to treat a patient (e.g., a human) that suffers from or is at risk of suffering from a disease, disorder, condition, or symptom caused by or related to ASCT2 functional abnormality, including, but not limited to, cancer, microbial infections, and ischemia-related central nervous system injuries. The compounds of the invention can be used alone or in combination with other agents and compounds to treat such diseases, disorders, conditions, and symptoms. Each such treatment described herein includes the step of administering to a patient in need thereof a therapeutically effective amount of a compound of the invention described herein to delay, reduce or prevent such disease, disorder, condition, or symptom.

Besides being useful for human treatment, the compounds and formulations of the present invention are also useful for the treatment of ASCT2 functional abnormality in animals, e.g., the veterinary treatment of domesticated animal, companion animals (e.g., dogs and cats), exotic animals, farm animals (e.g., ungulates, including horses, cows, sheep, goats, and pigs), and animals used in scientific research (e.g., rodents).

It is known that ASCT2 plays a role in several disease processes, including cancer and ischemia-related central nervous system injuries. Accordingly, inhibition of ASCT2 is known to be effective to prevent or treat these disease processes. For example, targeting the ASCT2 transporter has been identified as a therapy to inhibit cancer cells (reviewed in: Nakanishi et al., J. Pharm. Sci. 100:3731 (2011)). Antisense mRNA to specifically down-regulate ASCT2 effectively inhibits survival of human hepatoma cells (Fuchs et al., Am. J. Physiol. Cell. Physiol. 293 C55 (2007)).

The involvement of ASCT2 glutamine transport abnormality or dysfunction is involved in a broad spectrum of cancer types and subtypes. For example, glutamine metabolism and glutamine transport by the ASCT2 transporter is up-regulated in a wide variety of tumor cell types, which gives them a growth advantage over normal cells (Fuchs et al., Sem. Cancer Biol., 15:254-266 (2005)). Specifically, ASCT2 was upregulated (statistically significant) in brain, colon, eye, kidney, liver, lung, lymph node, mammary gland, muscle, pancreas, placenta, skin, and stomach. Other studies show the broad expression and dependence of various cancer cells on the obligate glutamine transporter ASCT2, such as in breast cancer (Collins et al., J. Cell Physiol., 176:166-178 (1998)) and colon carcinoma (Wasa et al., Ann. Surg., 22:189-97 (1996)).

Ischemia-Related Central Nervous System Injury

It is known that ASCT2 glutamine transport abnormalities also play a role in ischemia-related central nervous system injuries. For example, Wolosker et al. (FEBS Journal, 275: 3514-3526 (2008)) describes the role that glutamate transporters play in the regulation of NMDAR receptors. NMDAR receptor activity has been correlated with neuronal damage following ischemia (i.e., stroke). One way to control NMDAR activity is to limit the availability of its agonist ligand, D-serine. Glutamate ASCT 2 inhibition, as provided by the compounds and methods of the present invention, limits the level of D-serine available to NMDAR receptors, thereby limiting NMDAR activity and conferring a neuroprotective benefit.

In other embodiments of the present invention, the compounds disclosed herein are also useful for the treatment of ASCT2 functional abnormality in animals, e.g., the veterinary treatment of domesticated animal, companion animals (e.g., dogs and cats), exotic animals, farm animals (e.g., ungulates, including horses, cows, sheep, goats, and pigs), and animals used in scientific research (e.g., rodents).

Methods of Diagnostic Imaging

Compounds of the invention that contain a radionuclide, such as fluorine-18, can also be used, alone or in combination with other agents and compounds, in radiographic medical imaging applications in a patient (e.g., a human) to diagnose or follow the progression of diseases, disorders, conditions or symptoms related to a disease, disorder, condition, or symptom caused by or related to ASCT2 functional abnormality, including, but not limited to, cancer, microbial infections, and ischemia-related central nervous system injuries. This use of ASCT2 inhibitors is shown in US Published Patent Application No. 2015/0056138, incorporated herein by reference. Radiologists and other medical clinicians are skilled in the use of radiographic imaging devices, such as positron emission tomography (PET) scanners, and methods of imaging diagnostic compounds, such as the radionuclide compounds of the invention, in a patient are widely known (e.g., Saha, Basics of PET Imaging: Physics, Chemistry, and Regulations, Springer (2010) ISBN 978-1-4419-0804-9, hereby incorporated by reference).

The radionuclide compounds and formulations of the present invention are also useful for the medical imaging of animals, e.g., the veterinary treatment of domesticated animal, companion animals (e.g., dogs and cats), exotic animals, farm animals (e.g., ungulates, including horses, cows, sheep, goats, and pigs), and animals used in scientific research (e.g., rodents and non-human primates).

Methods of Radionuclide Compound Synthesis

The radionuclide diagnostic compounds of the invention can be synthesized by several techniques known to persons skilled in the art. For example, for the substitution of a carbon atom by a carbon-11, several derivatives such as [$^{11}$C]methyl iodide or [$^{11}$C]methyl triflate (Welch et al., In Handbook of Radiopharmaceuticals-Radiochemistry and Applications (Welch M J, Redvanly C S Eds.), New York-Chichester-Brisbane-Toronto, Wiley-Interscience Pub., 1-848 (2003)).

In the case of a labeling with fluorine-18, the radioisotope may be directly attached to a core structure by nucleophilic aliphatic or aromatic (including heteroaromatic (Dolle et al., Curr. Pharm. Design 11:3221-3235 (2005)) substitutions or electrophilic substitutions or linked through the addition of a spacer group, both techniques known to persons skilled in the art (Kilbourn, In fluorine-18 Labeling of Radiopharmaceuticals, Nuclear Science Series (Kilbourn M R Ed.), National Academy Press, Washington, D.C., 1-149 (1990); Lasne et al., Topics in Current Chemistry 222:201-258 (2002); Cai et al., Eur. J. Org. Chem. 17:2853-2873 (2008); and Dolle et al., In Fluorine and Health: Molecular Imaging, Biomedical Materials and Pharmaceuticals, Tressaud A, Haufe G (Eds). Elsevier 3-65 (2008)). An alkyl, alkenyl or alkynyl linker may also be used for the addition of the fluorine-18 atom (Damont et al., J. Label. Compds Radiopharm. 51:286-2.92 (2008); Dolle et al., Bioorg. Med. Chem. 14:1115-1125 (2006); and Dolle et al., J. Label. Compds Radiopharm. 50:716-723 (2007)). Additional methods of producing radionuclide (e.g., fluorine-18) labeled compounds are described in U.S. Patent Application Publications No. 2006/0100465, 2010/0292478, and 2011/0184159, each hereby incorporated by reference.

In the case of a labeling with other halogens (e.g., bromine-76, iodine-123 or iodine-124), the radioisotope may also be directly attached by nucleophilic or electrophilic substitutions to a core structure or linked through the addition of a spacer group, both techniques known to persons skilled in the art (Maziere et al., Curr. Pharm. Des. 7:1931-1943 (2001); and Coenen et al. In Radioiodination reactions for pharmaceuticals-Compendium for effective synthesis strategies, Coenen H. H., Mertens J., Maziere B. (Eds), Springer Verlag, Berlin-Heidelberg, 1-101 (200006)).

In the case of the labeling with metal radioisotopes (e.g., gallium-68, copper-64 or technetium-99m), the preferred approach used, which will be considered by a person skilled in the art, is the use of a bifunctional chelating agent based on, for example, the open-chain polyaminocarboxylates ethylenediamine tetraacetic acid (EDTA) and diethylenetriamine pentaacetic acid (DTPA), the polyaminocarboxylic macrocycle 1,4,7,10-tetraazacyclododecane-1,4,7,10-tetraacetic acid (DOTA), mercaptoacetyldi- and triglycine (MAG2. MAG3), bis-(S-benzoyl-thioglycoloyl)diaminopropanoate ((SBT)$_2$DAP) and hydrazinonicotinic acid (HYNIC), facilitating the complexation of the radiometal cation at one function and the covalent attachment to a core molecule at another (Brunner et al., (1995) Radiotracer production-Radiometals and their chelates In Principle of Nuclear Medecine, Wagner H. N. (Ed). Saunders: Philadelphia, 220-228 (1995); Weiner R. E. et al., Chemistry of gallium and indium radiopharmaceuticals In Handbook of Radiopharmaceuticals-Radiochemistry and Applications (Welch M J, Redvanly C S Eds.), New York-Chichester-Brisbane-Toronto, Wiley-Interscience Pub., 363-400 (2003); Anderson et al., Chemistry of copper radionucleides and radiopharmaceutical products In Handbook of Radiopharmaceuticals—Radiochemistry and Applications (Welch M J, Redvanly C S Eds.), New York-Chichester-Brisbane-Toronto. Wiley-Interscience Pub., 401-422 (2003); and Mahmood et al., Technetium radiopharmaceuticals In Handbook of Radiopharmaceuticals—Radiochemistry and Applications (Welch M J, Redvanly C S Eds.), New York-Chichester-Brisbane-Toronto, Wiley-Interscience Pub., 323-362 (2003)).

The diagnostic compounds of the invention described herein that include a radionuclide (e.g., fluorine-18) can be synthesized to adjust the specific activity of the compound. Specific activity is defined as the radioactivity per unit mass of a radionuclide or a labeled compound. For example, if a 50 mg sample contains 100 mCi (370 MBq), then the specific activity of the sample is given as 100/50=2 mCi/mg or 74 MBq/mg. Specific activity should not be confused with the concentration of a compound containing a radionuclide, which are generally expressed in mCi/mL or MBq/mL. The specific activity is an important parameter to consider in radiolabeling and in vivo biodistribution of tracers, such as the radionuclide compounds of the invention. Cold molecules in low specific activity radiopharmaceuticals compete with radioactive molecules and lower the uptake of the tracer in the target tissue(s). Similarly, low specific activity radionuclides yield poor radiolabeling, and hence, poor radiography (e.g., PET). For these reasons, the diagnostic compounds of the invention containing fluorine-18 are synthesized having a specific activity of at least 1.0, 1.2, 1.4, 1.8, 2.0, 2.2, 2.4, or 2.6 Ci/mmol. In one embodiment of the invention, the fluorine-18 diagnostic compound has a specific activity of at least 1.0 Ci/mmol.

Persons having skill in the art are aware of methods that can increase or decrease the specific activity of a desired radionuclide compound of the invention. For example, electrophilic fluorination of palladium aryl complexes can be used to yield diagnostic compounds of the invention containing fluorine-18 with high specific activity (Lee et al., (2011)).

Co-Administration

The invention further relates to the use of a first amount of an ASCT2 inhibitor of the present invention and a second amount of an anti-cancer agent in a method of treating cancer.

In particular embodiments of this invention, the combination of a compound of the present invention is anti-cancer agent is additive, i.e. the combination treatment regimen produces a result that is the additive effect of each constituent when it is administered alone. In accordance with this embodiment, the amount of an ASCT2 inhibitor of the present invention and the amount of the anti-cancer together constitute an effective amount to treat cancer.

In another particular embodiment of this invention, the combination of a compound of the present invention and anti-cancer agent is considered therapeutically synergistic when the combination treatment regimen produces a significantly better anticancer result (e.g., cell growth arrest, apoptosis, induction of differentiation, cell death) than the additive effects of each constituent when it is administered alone at a therapeutic dose. Standard statistical analysis can be employed to determine when the results are significantly better. For example, a Mann-Whitney Test or some other generally accepted statistical analysis can be employed.

The treatment procedures can take place sequentially in any order, simultaneously or a combination thereof. For example, the first treatment procedure, administration of a compound of the present invention, can take place prior to the second treatment procedure, i.e. the anti-cancer agent, after the second treatment with the anticancer agent, at the same time as the second treatment with the anticancer agent, or a combination thereof. For example, a total treatment period can be decided for the compound of the present invention. The anti-cancer agent can be administered prior to onset of treatment with the compound of the present invention or following treatment with a compound of the present invention. In addition, treatment with the anti-cancer agent can be administered during the period of administration of the compound of the present invention but does not need to occur over the entire treatment period for the ASCT2 inhibitor of the present invention. Similarly, treatment with the compound of the present invention can be administered during the period of anti-cancer agent administration but does not need to occur over the entire anti-cancer agent treatment period. In another embodiment, the treatment regimen includes pre-treatment with one agent, either the compound of the present invention or the anti-cancer agent, followed by the addition of the second agent for the duration of the treatment period.

Non-limiting examples of anticancer compounds of the present invention include compounds selected from carboplatin, gemcitabine, cisplatin, 5-fluorouracil, cyclophosphamide, etoposide, vincristine, doxorubicin and irinotecan.

Experimental/Examples

The following examples are present to provide those of ordinary skill in the art with a more complete disclosure and description of how compounds of the present invention are made and used and are intended to be purely exemplary of the present invention and are not intended to limit the scope of what the inventors regard as their invention.

Methods of Making Examples of the Present Invention

An examples of methods of making compounds of the present invention is structure-based design with technology-enabled medicinal chemistry and high-throughput screening to identify novel ASCT2 probes with improved potency that explore the steric environment of the ASCT2 amino acid binding pocket. Since the crystal structure of human ASCT2 has not been elucidated, the present inventors leveraged computational approaches similar to the approach of Albers et. al. (Mol. Pharmacol.; 2012, 81 (3) 356-365) to explore potential points of intermolecular interaction and binding pockets accessible to candidate substrates and inhibitors. From a homology model based on the inhibited structure of the bacterial aspartate transporter GltPh in complex with inhibitor D,L-threo-benzyloxyaspartate (TBOA); PDB ID 2NWW, targetable structural motifs were identified including a lipophilic pocket adjacent to the amino acid zwitterion binding site and potential hydrophilic points of contact in a loop region displaced by the inhibitor in the open form of the transporter. Based upon these structural elements, the present inventors expanded a focused library of candidate small molecules based on the Nγ-glutamylanilide series to generate examples of compounds of the present invention with enhanced structure activity relationships toward development of more potent ASCT2 inhibitors.

Previously reported syntheses of GPNA and related analogs required 6 steps starting from L-glutamate in overall yields ranging from 10-54%. In order to achieve a more facile synthesis, we took advantage of microwave-assisted organic synthesis (MAOS) to rapidly generate GPNA analogs in just two steps starting from commercially available Boc-L-glutamic acid-tert-butyl ester with yields ranging from 23-75% over two steps. See the scheme below:

Previously reported synthesis of glutamyl anilides

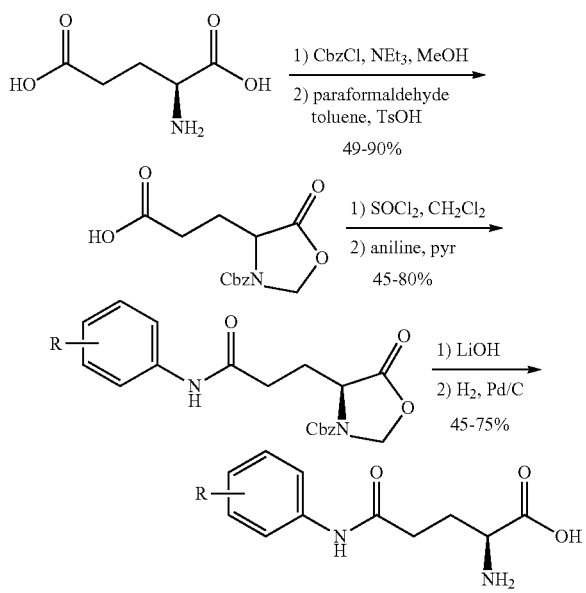

Microwave-assisted synthesis of glutamyl anilides

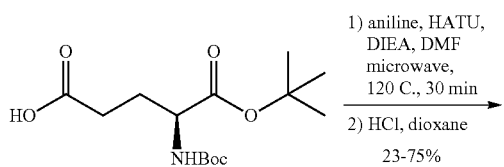

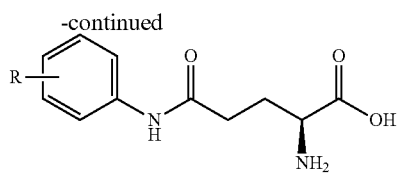

Initial compound libraries focused on 2, 3, and 4 substituted Nγ-glutamylanilides with aryl, alicyclic, and heterocyclic substitutions. To evaluate the biological activity, compounds were initially screened at a single concentration for their ability to inhibit $^3$H-glutamine uptake in live HEK-293 cells, an established model suitable for evaluating ASCT2 activity. Full concentration response curves were developed for compounds that exhibited evidence of glutamine inhibition; inactive compounds were not pursued further. The present inventors prioritized the 2-substitution as a determinant of ASCT2 activity among this series. For example, N-(2-morpholinophenyl)-L-glutamine (Table 1, compound 3) emerged as a potential lead compound of interest, exhibiting a potency roughly equivalent to that of GPNA (Table 1, compound 1). 4-morpholinophenyl and 3-morpholinophenyl anilides proved to exhibit lesser activity, leading us to pursue 2-substituted glutamyl anilides as initial lead compounds. Further development of the 2-substituted series led to three particular examples of the present invention with significantly greater potency than GPNA, $N^5$-(2-(benzo[d]thiazol-2-yl)phenyl)-L-glutamine (Table 1, compound 4), N-(2-(morpholinomethyl)phenyl)-L-glutamine (Table 1, compound 5)[17], and N5-(2-((4-methylpiperazin-1-yl)methyl)benzyl)-L-glutamine (Table 1, compound 20). Furthermore, 4 novel compounds among the series exhibited potencies equivalent to GPNA.

TABLE 1

| Compound | | $IC_{50}$ |
|---|---|---|
| 1 | ![structure] | 954 μM |
| 2 | ![structure] | ** |
| 3 | ![structure] | 664 μM |

TABLE 1-continued
| Compound | | IC$_{50}$ |
|---|---|---|
| 4 | 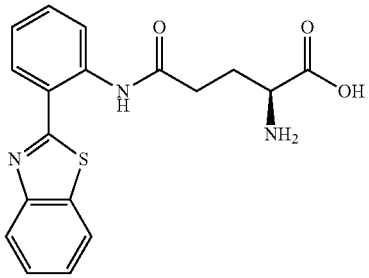 [SMILES: N[C@@H](CCC(=O)Nc1ccccc1-c1nc2ccccc2s1)C(=O)O] | 436 µM |
| 5 | 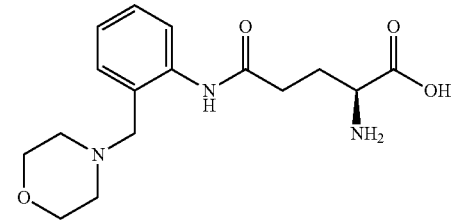 [SMILES: N[C@@H](CCC(=O)Nc1ccccc1CN1CCOCC1)C(=O)O] | 312 µM |
| 6 | 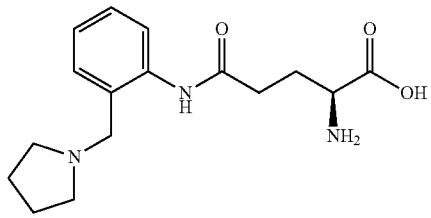 [SMILES: N[C@@H](CCC(=O)Nc1ccccc1CN1CCCC1)C(=O)O] | ** |
| 7 | 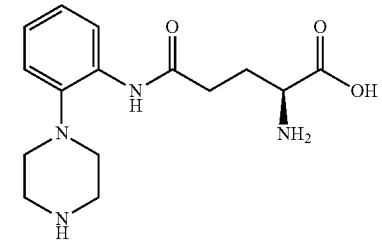 [SMILES: N[C@@H](CCC(=O)Nc1ccccc1N1CCNCC1)C(=O)O] | ** |
| 8 | 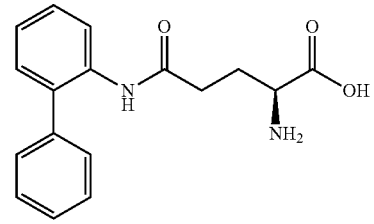 [SMILES: N[C@@H](CCC(=O)Nc1ccccc1-c1ccccc1)C(=O)O] | ** |
| 9 | 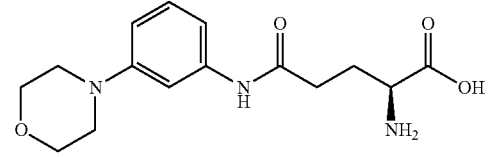 [SMILES: N[C@@H](CCC(=O)Nc1cccc(N2CCOCC2)c1)C(=O)O] | ** |

TABLE 1-continued
| Compound | | IC$_{50}$ |
|---|---|---|
| 10 | 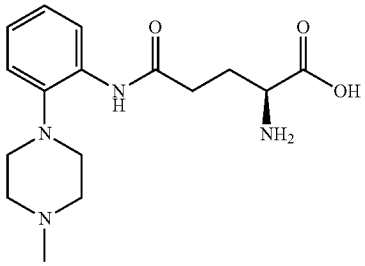 [SMILES: CN1CCN(c2ccccc2NC(=O)CC[C@H](N)C(=O)O)CC1] | ** |
| 11 | 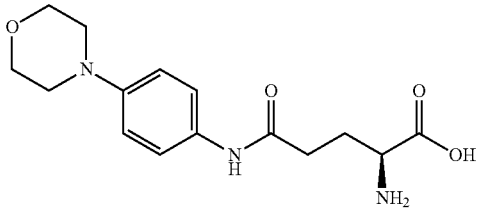 [SMILES: N[C@@H](CCC(=O)Nc1ccc(N2CCOCC2)cc1)C(=O)O] | ** |
| 12 | 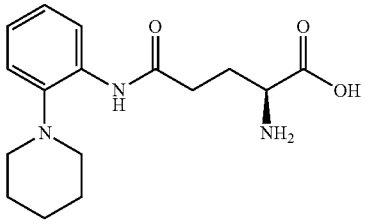 [SMILES: N[C@@H](CCC(=O)Nc1ccccc1N1CCCCC1)C(=O)O] | 776 μM |
| 13 | 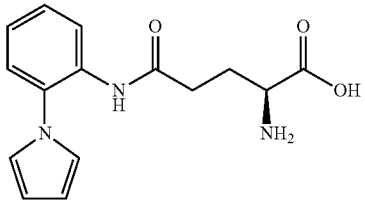 [SMILES: N[C@@H](CCC(=O)Nc1ccccc1-n1cccc1)C(=O)O] | ** |
| 14 | 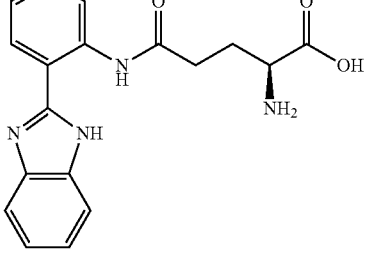 | ** |
| 15 | 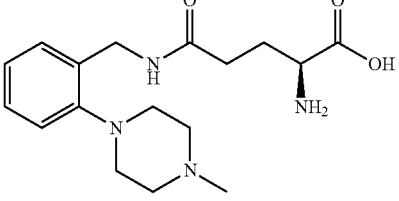 | ** |

TABLE 1-continued

| Compound | | IC$_{50}$ |
|---|---|---|
| 16 | [structure] | 832 μM |
| 17 | [structure] | ** |
| 18 | [structure] | ** |
| 19 | [structure] | 677 μM |
| 20 | [structure] | 697 μM |

Biologically active compounds were also evaluated computationally in the open human ASCT2 model. The best scoring poses for the most potent compounds identified demonstrated a compatible fit with the human ASCT2 model and, interestingly, a tendency to exhibit points of interaction with both the amino acid zwitter ion binding site and an adjacent hydrophobic pocket.

General Procedure for the Synthesis of N$_2$-Glutamylanilides:

To a microwave vial containing a solution of Boc-L-glutamic acid tert-butyl ester (0.165 mmol, 1.0 eq) and HATU (0.165 mmol, 1.0 eq) in DMF (1.65 mL) was added the amine followed by DIPEA (57.5 μL, 2.0 eq). The vial was sealed and heated under microwave irradiation for 30 min at 120° C. Upon completion, the reaction was partitioned between water and CH$_2$Cl$_2$, extracted 3× with CH$_2$Cl$_2$, dried over anhydrous Na$_2$SO$_4$ and concentrated under vacuum. Compounds were purified via reverse phase chromatography (5-95% acetonitrile/water) to afford the N-boc-glutamylanilide-tert-butyl esters. The compounds were transferred to vials followed by the addition of 2.0 mL of 4.0M HCl in dioxane. The reaction stirred at 40° C. for 4 hours. The reactions were concentrated under vacuum to afford the title compounds which were used without further purification.

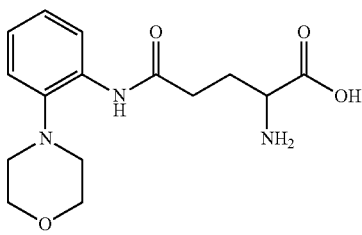 [SMILES: NC(CCC(=O)Nc1ccccc1N1CCOCC1)C(=O)O]

The above compound was prepared according to the general procedure. 1H NMR (400 MHz, CD$_3$OD) δ (ppm): 7.85 (d, J=7.9 Hz, 1H); 7.62-7.50 (m, 3H); 4.19-4.09 (m, 5H); 3.78-3.71 (m, 4H); 3.05-2.89 (m, 2H); 2.45-2.27 (m, 2H). 13C NMR (100 MHz, CD$_3$OD) δ (ppm): 175.69; 171.37; 132.17; 132.07; 129.32; 127.35; 123.22; 73.56; 72.45; 62.18; 55.93; 53.24; 43.75; 32.65; 26.59.

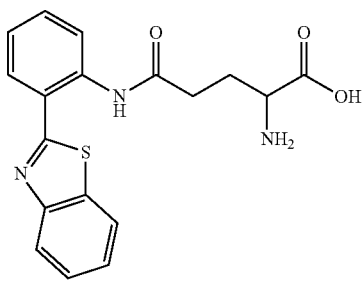 [SMILES: NC(CCC(=O)Nc1ccccc1-c1nc2ccccc2s1)C(=O)O]

The above compound was prepared according to the general procedure. 1H NMR (400 MHz. CD$_3$OD) δ (ppm): 8.62 (d, J=8.1 Hz, 1H); 8.12 (d, J=8.1 Hz, 1H); 8.06 (d, J=7.8 Hz, 1H); 8.01 (dd, J1=7.9 Hz, J2=1.4 Hz, 11H); 7.59 (td, J1=7.1 Hz, J2=1.2 Hz, 1H); 7.52 (qd, J1=8.4 Hz, J2=1.5 Hz, 2H); 7.28 (td, J=7.0 Hz, J2=1.1 Hz, 1H); 4.16 (t, J=6.5 Hz, 1H); 2.95-2.84 (m, 2H); 2.47-2.29 (m, 2H). 13C NMR (100 MHz, CD$_3$OD) (ppm): 171.05; 170.06; 168.39; 152.56; 137.00; 133.31; 131.55; 129.77; 126.62; 125.90; 123.87; 122.36; 121.42; 121.12; 119.91; 52.00; 32.95; 25.57.

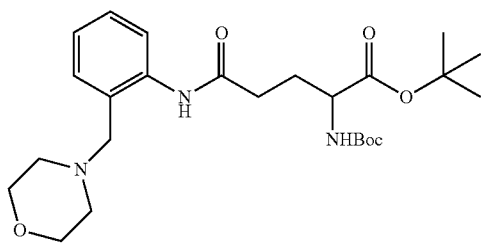 [SMILES: CC(C)(C)OC(=O)NC(CCC(=O)Nc1ccccc1CN1CCOCC1)C(=O)OC(C)(C)C]

The above compound was prepared according to the general procedure. 1H NMR (400 MHz. CD$_3$OD) δ (ppm): 7.64 (d, J=7.61, 1H); 7.56 (td. J1=7.6 Hz, J2=1.1 Hz, 1H); 7.46-7.40 (m, 2H); 4.39 (s, 2H); 4.13 (t, J=6.6 Hz, 1H); 4.05 (dd. J1=12.7 Hz, J2=2.4 Hz, 2H); 3.82 (t, J=12.1 Hz, 2H); 3.42 (d. J=12.3 Hz); 2.96-2.81 (m, 2H); 2.41-2.24 (m, 2H). 13C NMR (100 MHz, CD$_3$OD) δ (ppm): 173.34; 169.98; 136.88; 133.03; 131.06; 127.37; 127.19; 124.24; 63.59; 56.59; 51.89; 51.52; 51.48; 30.99; 25.26.

Glutamine Uptake:

The glutamine uptake assays in HEK293 cells were carried out in 96 well plates (CulturPlate-96, Perkin Elmer). Cells were plated at a density of 35,000 cells per well 24 hours prior to carrying out the assay. Each set of conditions is carried out in triplicate. The wells are washed three times with 100 uL of assay buffer at pH 6.0 (containing 137 mM NaCl, 5.1 mM KCl, 0.77 mM KH$_2$PO$_4$, 0.71 mM MgSO$_4$.7H$_2$O, 1.1 mM CaCl$_2$, 10 mM D-glucose, and 10 mM HEPES). $^1$H-glutamine (500 nM) in the same buffer is added along with inhibitor and allowed to incubate for 15 min at 37° C. Following incubation, the H-glutamine/inhibitor is removed and the cells are washed three times with buffer. The cells are then lysed by the addition of 50 uL 1M NaOH. 150 uL of scintillation fluid (Microscint 40, Perkin Elmer) is added and the plates are counted on a scintillation counter (Topcount, Perkin Elmer).

A model of an inhibitor-bound conformation of human ASCT2 was used as a target for ligand docking of proposed compounds in the 2-substituted Nγ-glutamylanilide series using SurflexDock v.2.706 from Biopharmics (Jain et al. J. Med. Chem. 2003, 46, 499-511) as implemented in Tripos' SYBYL-X v2.1 (Certera, 1699 South Hanley Rd. St. Louis, Mo. 63144-2917; http://www.certara.com). Additionally, all compounds were experimentally tested for their potency in inhibition of the uptake of [3H]-glutamine in a plate-based assay. Compounds with potency values equal to or better than the inhibitor GPNA were retained and assessed for their fit into the homology model of human ASCT2 to facilitate design of further ligand series in an attempt to discover structure activity relationships for development of potent inhibitors of ASCT2-mediated transport of [3H]-glutamine. Two-dimensional structures for all ligands were generated in ChemDraw and imported into Tripos Sybyl for conversion into three-dimensional structures using CONCORD and docking using SurflexDock (referenced above). Figures for docked complexes were generated and ray-traced using PyMol (The PyMOL Molecular Graphics System, Version 1.5.0.4, Schrödinger, LLC.).

Throughout this application, and specifically in the list below, various references are cited. All such references are incorporated herein by reference in their entirety.

Dang, C. V. *Cancer Research*, 2010, 70, 859.

Dang, C. V.; Le, A.; Gao, P. *Clinical Cancer Research*, 2009, 15, 6479.

Watanabe, T.; Kobunai, T.; Yamamoto, Y.; Matsuda, K.; Ishihara, S.; Nozawa, K.; Iinuma, H.; Ikeuchi, H.; Eshima, K. *Eur. J. Cancer*, 2011, 47, 1946.

Gaglio, D.; Metallo, C. M.; Gameiro, P. A.; et al. *Molecular systems biology*, 2011, 7, 523.

Shimizu, K.; Kaira, K.; Yomizawa, Y.; Sunaga, N.; Kawashima, O.; Oriuchi, N.; Tominaga, H.; Nagamori, S.; Kanai, Y.; Yamada, M.; Oyama, T.; Takeyoshi, I. *British Journal of Cancer*, 2014, 110, 2030-2039.

Witte, D.; Ali, N.; Carlson, N.; Younes, M. *Anticancer Res.*, 2002, 22(3), 2555-2557.

Kaira, K.; Sunrose, Y.; Arakawa, K.; Sunaga, N.; Shimizu, K.; Tominaga, H.; Oriuchi, N.; Nagamori, S.; Kanai, Y.; Oyama, T.; Takeyoshi, I. *Histopathology*, 2014, ahead of print.

Fuchs, B. C.; Perez, J. C.; Suetterlin, J. E.; Chaudhry, S. B.; Bode, B. P. *Am. J. Physiol. Gastrointest. Liver Physiol.* 2004, 286(3), G467-G478.

Hassanein, M.; Hoeksema, M. D.; Shiota, M.; Qian, J.; Harris, B. K.; Chen, H.; Clark, J. E.; Alborn, W. E.; Eisenberg, R.; Massion, P. P. *Clin. Cancer Res.* 2013, 19(3), 560-570.

Esslinger, C. S.; Cybulski, K. A.; Rhoderick, J. F. *Biooorg. Med. Chem.*, 2005, 13, 1111-1118.

Albers, T.; Marsiglia, W.; Thomas, T.; Gameiro, A.; Grewer, C. *Mol. Pharmacol.;* 2012, 81(3), 356-365.

14. Brown, J. M.; Hunihan, L.; Prack, M. M.; Harden, D. G.; Bronson, J.; Dzierba, C. D.; Gentles, R. G.; Hendricson, A.; Krause, R.; Macor, J. E.; Westphal, R. S. *J. Neurochem.;* 2014, 129(2), 275-283.

The invention claimed is:

1. A compound of the following formula:

wherein:
- $R^1$ is a bond, optionally substituted $C_1$-$C_6$ alkyl, or optionally substituted —($C_1$-$C_6$ alkyl)—$SO_2$—$R^2$;
- $R^2$ is optionally substituted and chosen from morpholino, pyrrolidine, pyrrole, piperidine, pyridine, benzoimidazole, benzothiazole, piperazine, methyl-piperazine;
- $R^3$ is H or optionally substituted $C_1$-$C_6$ alkyl; and
- $R^4$ is $NH_2$ or NHBoc;

or pharmaceutically acceptable salts thereof.

2. A compound of claim 1, wherein $R^1$ is a bond, —$CH_2$—, or —$CH_2$—$CH_2$—.

3. A compound of claim 1, wherein $R^2$ is chosen from:

4. A compound of claim 1, wherein $R^3$ is —H or

5. A compound of claim 1, of the following formula:

or a pharmaceutically acceptable salt thereof.

6. A method of modulating ASCT2 function in a patient in need thereof, comprising administering to the patient an effective ASCT2 function modulating amount of a compound of claim 1.

7. A method of modulating angiogenesis, tumor progression, and/or metastasis comprising the step of administering a compound of claim 1 to a tissue or a subject associated with a disease condition in a therapeutically effective amount to inhibit cellular glutamine uptake via ASCT2.

8. A pharmaceutical composition, comprising a compound of claim 1 and a pharmaceutically acceptable carrier.

9. A compound comprising:
   a compound of claim 1 and an imaging agent coupled thereto.

10. A compound of claim 9, wherein the imaging agent is a radionuclide.

11. A method of ameliorating a cancer influenced by abnormal ASCT2 transporter dysfunction, comprising administering to a subject in need thereof an effective ASCT2 function inhibiting amount of a compound of the following formula:

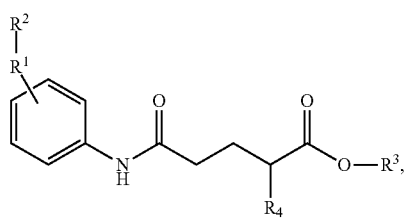

wherein:
   $R^1$ is a bond, optionally substituted $C_1$-$C_6$ alkyl, or optionally substituted —($C_1$-$C_6$ alkyl)—$SO_2$—$R^2$;
   $R^2$ is optionally substituted and chosen from morpholino, pyrrolidine, pyrrole, piperidine, pyridine, benzoimidazole, benzothiazole, piperazine, methyl-piperazine;
   $R^3$ is H or optionally substituted $C_1$-$C_6$ alkyl; and
   $R^4$ is $NH_2$ or NHBoc;
or pharmaceutically acceptable salts thereof; to thereby treat cancer.

12. The method of claim 11, wherein the cancer is lung, colon, or pancreas cancer.

13. The method of claim 11, wherein the compound is of the following formula:

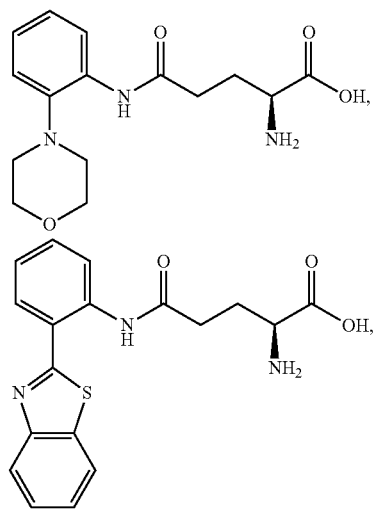

-continued

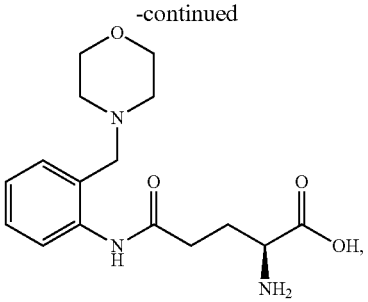

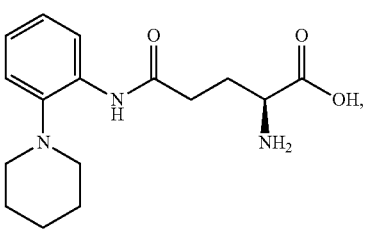

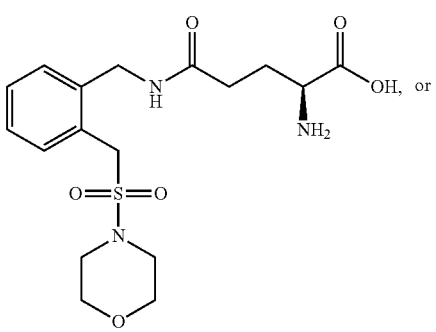

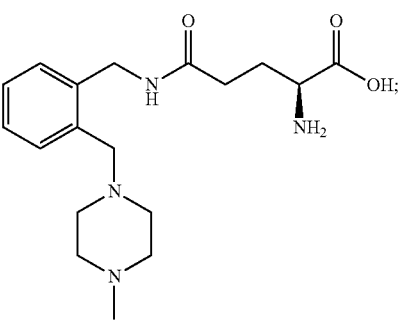

or a pharmaceutically acceptable salt thereof.

* * * * *